United States Patent
Chalekian et al.

(10) Patent No.: US 9,254,191 B2
(45) Date of Patent: Feb. 9, 2016

(54) BALLOON EXPANDABLE PLATFORM WITH RETAINING FEATURES FOR A COLLAPSIBLE VALVE

(75) Inventors: Aaron J. Chalekian, Minneapolis, MN (US); Daniel J. Klima, Andover, MN (US); Cherry L. Knight, New Hope, MN (US); Jane M. Korfe, Buffalo, MN (US); Trevor C. Knight, Minnetonka, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 109 days.

(21) Appl. No.: 13/698,162

(22) PCT Filed: May 19, 2011

(86) PCT No.: PCT/US2011/000892
§ 371 (c)(1),
(2), (4) Date: Jan. 14, 2013

(87) PCT Pub. No.: WO2011/146124
PCT Pub. Date: Nov. 24, 2011

(65) Prior Publication Data
US 2013/0218266 A1  Aug. 22, 2013

Related U.S. Application Data

(60) Provisional application No. 61/346,175, filed on May 19, 2010.

(51) Int. Cl.
*A61F 2/95* (2013.01)
*A61F 2/24* (2006.01)
*A61F 2/958* (2013.01)
*A61M 25/10* (2013.01)

(52) U.S. Cl.
CPC .............. *A61F 2/2433* (2013.01); *A61F 2/958* (2013.01); *A61F 2002/9583* (2013.01); *A61F 2002/9586* (2013.01); *A61M 2025/1086* (2013.01)

(58) Field of Classification Search
CPC ... A61F 2002/9583; A61F 2/95; A61F 2/958; A61F 2/2433; A61M 2025/1086
USPC ......................................... 623/1.11; 606/194
See application file for complete search history.

(56) References Cited

U.S. PATENT DOCUMENTS

| | | | | |
|---|---|---|---|---|
| 5,935,135 A * | 8/1999 | Bramfitt et al. | ............... | 623/1.11 |
| 6,027,510 A * | 2/2000 | Alt | ................. | 606/108 |
| 6,106,530 A * | 8/2000 | Harada | ......................... | 623/1.11 |
| 6,468,299 B2 * | 10/2002 | Stack et al. | .................. | 623/1.11 |

(Continued)

OTHER PUBLICATIONS

Australian Examination Report for Application No. 2011256841 dated Sep. 17, 2013.

(Continued)

*Primary Examiner* — Sarah W Aleman
(74) *Attorney, Agent, or Firm* — Lerner, David, Littenberg, Krumholz & Mentlik, LLP

(57) ABSTRACT

Retainer structures (150) maintain stented valves (800) on the balloon (130) of a balloon catheter during delivery of the valve to an implantation node and subsequent expansion of the valve. The retainer structures define a raised edge relative to the outer surface of the balloon and limit movement of the valve longitudinally relative to the balloon. Deflation of the balloon following expansion of the valve stent releases the valve.

13 Claims, 7 Drawing Sheets

(56) References Cited

U.S. PATENT DOCUMENTS

| | | | |
|---|---|---|---|
| 6,569,192 B1 * | 5/2003 | Foreman | A61F 2/958 623/1.11 |
| 2002/0120321 A1 | 8/2002 | Gunderson et al. | |
| 2003/0074044 A1 * | 4/2003 | Randby et al. | 623/1.11 |
| 2003/0114915 A1 * | 6/2003 | Mareiro et al. | 623/1.11 |
| 2003/0199963 A1 * | 10/2003 | Tower et al. | 623/1.11 |
| 2004/0102791 A1 | 5/2004 | Murray | |
| 2004/0204749 A1 * | 10/2004 | Gunderson | 623/1.12 |
| 2006/0004439 A1 | 1/2006 | Spenser et al. | |
| 2007/0027534 A1 | 2/2007 | Bergheim et al. | |
| 2007/0288081 A1 | 12/2007 | Oepen et al. | |
| 2007/0293942 A1 | 12/2007 | Mirzaee | |

OTHER PUBLICATIONS

International Search Report for Application No. PCT/US2011/000892 dated Aug. 30, 2011.

Canadian Office Action for Application No. 2,799,610 dated Jan. 2, 2014.

* cited by examiner

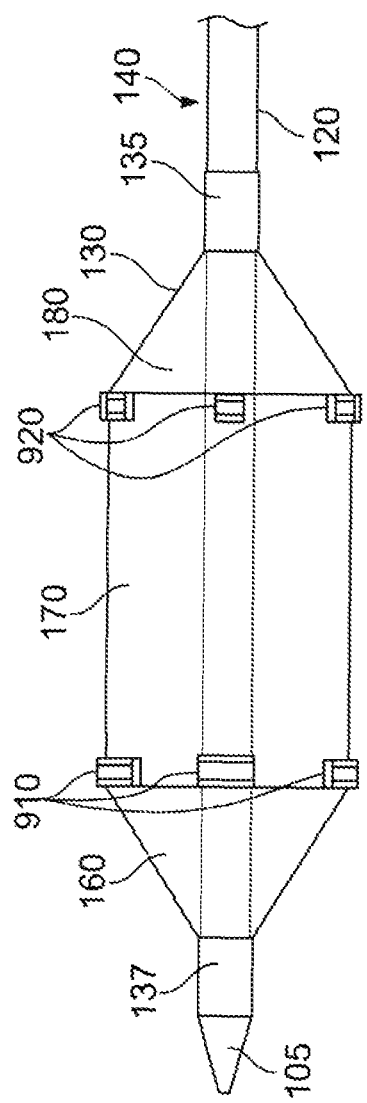

BALLOON EXPANDABLE PLATFORM WITH RETAINING FEATURES FOR A COLLAPSIBLE VALVE

CROSS-REFERENCE TO RELATED APPLICATION

The present application is a national phase entry under 35 U.S.C. §371 of International Application No. PCT/US2011/000892 filed May 19, 2011, published in English, which claims priority from U.S. Provisional Application No. 61/346,175, filed May 19, 2010, all of which are incorporated herein by reference.

BACKGROUND OF THE INVENTION

The present invention relates to collapsible prosthetic valves for use in heart valve repair. More particularly, the invention relates to methods and apparatus used to deploy balloon-expandable prosthetic valves.

Damaged or weak heart valves may require replacement with prosthetic valves. While prosthetic valves typically have been implanted using surgical procedures, recent developments in this area have led to prosthetic valves which are capable of implantation using minimally invasive techniques. One such technique employs valves supported by stents. Such valves may typically be collapsed into a compressed state for transluminal delivery to the desired location and then expanded in vivo for final placement. Devices for delivering these valves, such as catheter-based delivery devices, may be used to insert the valve through a body lumen of a human or animal, position the valve, release the valve within the body lumen, and, where necessary, expand the diameter of the valve to hold it in place in the body lumen.

Prosthetic valves may be self-expanding or may employ some other method, such as the application of heat or the inflation of one or more balloons, to facilitate expansion. Balloon expansion employs a catheter having a balloon which is inflated to expand the valve into the non-compressed state. Such balloons may be inflated by various methods, including providing gases or liquids to fill the interior space of the balloon. The balloon may subsequently be deflated to release the valve and to enable the balloon catheter to be withdrawn from the body.

In a typical balloon inflation arrangement, a prosthetic valve may be assembled over the uninflated balloon of a balloon catheter and then collapsed to a relatively small diameter, or may be slid over the uninflated balloon while collapsed to the relatively small diameter. A sheath of the catheter may then be positioned over the valve to hold it in place and maintain it in the collapsed condition. Once the catheter has been positioned at the desired location, the sheath may be removed, revealing the uninflated balloon and collapsed valve. The balloon may subsequently be inflated to expand the valve stent into contact with the body lumen. Once the valve has been properly placed and the valve stent fully expanded, the balloon may be deflated and the delivery catheter removed from the patient.

After removal of the sheath and prior to inflation of the balloon, several factors may make accurate positioning of the valve within the body lumen difficult. In particular, forces, such as the vibrations of a beating heart and the high velocity of blood flow within and immediately adjacent to the heart, create a turbulent environment which could cause the valve to move relative to the balloon during this time period. For example, the aforementioned forces may increase the likelihood that the valve will move longitudinally along the balloon. It will be appreciated that accurate location and expansion of the prosthetic valve is critical to the proper functioning of the valve. For example, if the valve were to move longintudinally relative to the balloon prior to balloon inflation, the valve may not be positioned in the correct location within the body lumen. Further, if the valve were to move so that the full length of the valve stent does not overlie the balloon when the balloon is inflated, the full length of the valve stent may not be expanded and the valve may not be securely held in place. Therefore, there exists a need for a device which will accurately maintain the position of the valve relative to the balloon during the deployment process.

SUMMARY OF THE INVENTION

One aspect of the present invention provides a delivery system for a prosthetic valve having a valve structure mounted to a stent structure. The stent structure may have a collapsed condition and an expanded condition. In the collapsed condition the stent may have a length between a first end and a second end.

The delivery system may also include a balloon extending in a longitudinal direction. The balloon has a first end portion, a second end portion, and a middle portion between the first end portion and the second end portion. The middle portion of the balloon has an outer surface with a first diameter in an inflated condition and a second diameter in a deflated condition. An inflation lumen may be connected in fluid communication to an interior of the balloon for supplying an inflation fluid to the balloon.

The delivery system may also include first and second retainer structures. Each of the retainer structures may define a raised edge relative to the outer surface of the middle portion. The raised edges may be spaced apart in the longitudinal direction to define a receiving space around the middle portion of the balloon. The receiving space may have a length in the longitudinal direction which is greater than the length of the stent structure in the collapsed condition. The entire length of the stent structure in the collapsed condition may be receivable in the receiving space. The raised edges may limit movement of the stent structure in the longitudinal direction relative to the balloon.

The first retainer structure may be of a type selected from the group consisting of a node, a ring, a skirt, and a fan skirt. The second retainer structure may be of a type selected from the group consisting of a node, a ring, a skirt, and a fan skirt. The first retainer structure may also be of a first type and the second retainer structure is of a type different from the first type. Alternatively, the first retainer structure may be of a first type and the second retainer structure may also be of the first type.

The raised edges may be positioned relative to the middle portion to limit movement of the stent structure in the longitudinal direction relative to the balloon when the balloon is in the inflated condition and the stent is in the expanded condition. The raised edges may be positioned relative to the middle portion to limit movement of the stent structure in the longitudinal direction relative to the balloon during inflation of the balloon from the deflated condition to the inflated condition. The raised edges may be sized and shaped to release the valve structure upon deflation of the balloon from the inflated condition.

Another aspect of the invention provides a method of delivering a prosthetic valve to an implantation site. The prosthetic valve may have a valve structure mounted to a stent structure. The stent structure may have a collapsed condition, an expanded condition, and a length in the collapsed condition between a first end and a second end. The method may include assembling the valve around a balloon having an inflated condition and a deflated condition. The balloon may extend in a longitudinal direction. The balloon may have an outer surface and first and second retainer structures each defining a raised edge relative to the outer surface. The raised edges may be spaced apart in the longitudinal direction to define a receiving space around the outer surface of the balloon. The receiving space may have a length in the longitudinal direction which is greater than the length of the stent structure in the collapsed condition. The valve may be assembled in the receiving space so that the stent structure is in the collapsed condition and the balloon is in the deflated condition.

The method may also include covering the valve in the collapsed condition and the balloon in the deflated condition with a sheath. The covered valve and balloon may be moved to an implantation site. The sheath may be removed from over the valve and the balloon to expose the valve and the balloon, whereby the valve is held in the receiving space and the raised edges limit movement of the stent structure in the longitudinal direction relative to the balloon. The balloon may be inflated to the inflated condition, whereby the stent structure of the valve is expanded to the expanded condition. The balloon may also be deflated to the deflated condition, and the deflated balloon may be removed from the stent structure.

The raised edges may limit movement of the stent structure in the longitudinal direction relative to the balloon when the balloon is in the inflated condition. The deflating step may release the stent structure from the receiving space so that the raised edges no longer limit movement of the stent structure in the longitudinal direction relative to the balloon. The removing step may include withdrawing the retainer structures through a lumen of the stent structure.

The first retainer structure may be of a type selected from the group consisting of a node, a ring, skirt, and a fan skirt. The second retainer structure may be of a type selected from the group consisting of a node, a ring, a skirt, and a fan skirt. The first retainer structure may be of a first type and the second retainer structure is of a type different from the first type. Alternatively, the first retainer structure is of a first type and the second retainer structure is of the first type.

BRIEF DESCRIPTION OF THE DRAWINGS

FIG. 9 is a partial side elevation view of a delivery catheter with an expanded balloon having a retaining mechanism in accordance with a sixth exemplary embodiment of the invention.

DETAILED DESCRIPTION

The present invention is directed to mechanisms for retaining a collapsible stented valve in place on a balloon catheter during a valve deployment procedure. Such mechanisms may include retaining structures which prevent or block the movement of the valve stent axially along the catheter balloon before the balloon has been fully inflated. The retaining structures may take various forms, including bulges, nodes, rings, skirts, or fans, and any combination of such forms. In some embodiments, when the balloon is fully inflated, each retaining structure may maintain its shape, preventing the valve stent from moving in the axial direction along the balloon. The valve may then be released upon deflation of the balloon. In some embodiments, the valve may be maintained in a position by a retaining structure as well as by the balloon during inflation, while in other embodiments, after initial expansion, the valve may be maintained in a position by only the balloon.

Figure 8:
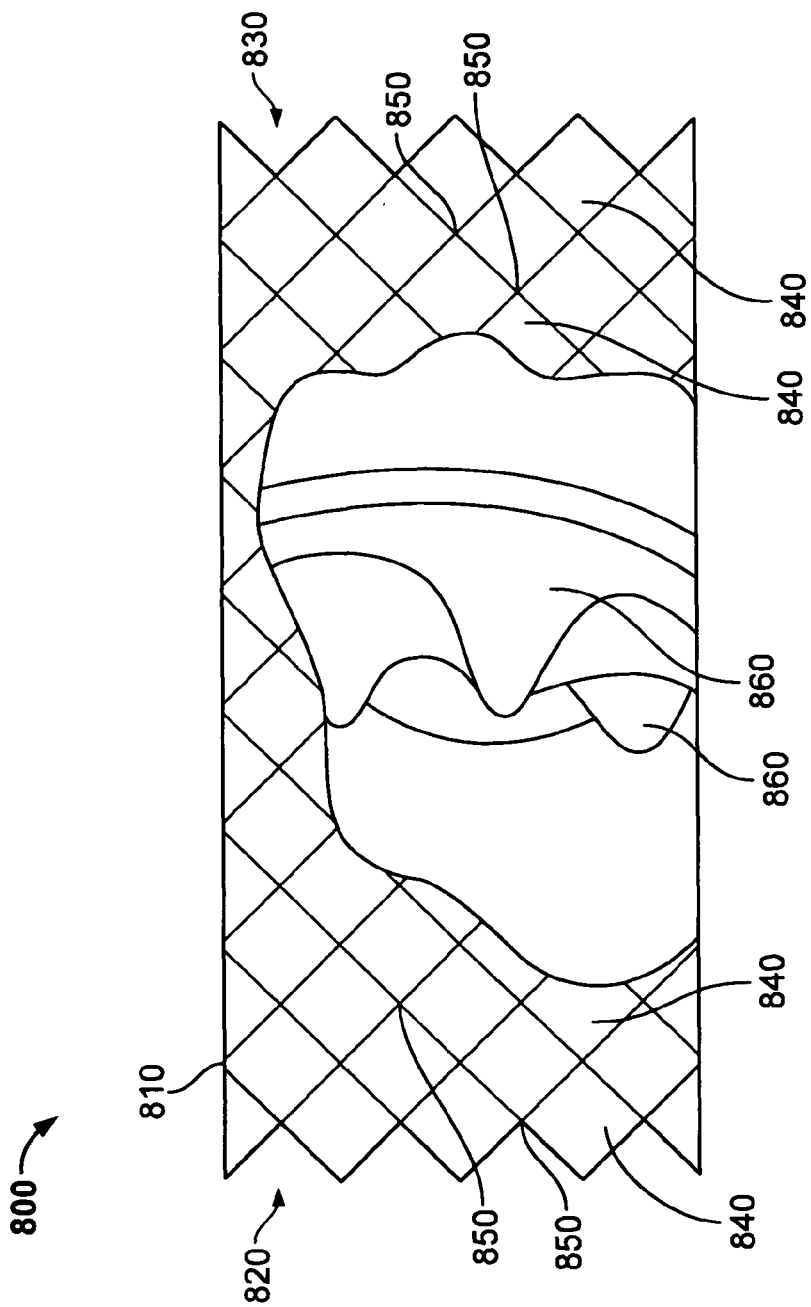
FIG. 8 is a highly schematic side elevational view of a stented valve, partially broken away to show the valve leaflets in the interior thereof.

The present invention may be used in connection with any suitable balloon-expandable stented valve. As presently known, and as depicted in FIG. 8, a conventional stented valve 800 includes a generally cylindrical stent 810 having a first end 820 and a second end 830, with a plurality of leaflets 860 supported within the stent. A plurality of interconnected struts 850 define cell structures 840 which enable stent 810 to collapse from the fully expanded diameter shown in the figure to a smaller collapsed diameter. In one example, struts 850 may be formed from a plurality of interconnected wires. In another example, the struts may be formed from a preformed tube which is cut to form the cell structures 840. Stent 810 may be formed from any biocompatible material that may be plastically deformed and that will retain its deformed shape.

Valve leaflets 860 may be formed from natural tissue, either human or animal, or from artificial materials, including polymers. Commissure posts and/or other stent structures may support valve leaflets 860 within stent 810.

The stent valves to which the present invention pertains may have a diameter of about 19 mm to about 27 mm when expanded for use in a body lumen. Such diameters may provide room for the valve within the stent and may also permit the stent valve to be held in place within the native valve architecture.

The valve may comprise two or more leaflets which alternate between open and closed positions with the change in flow pressure of blood. In particular, the leaflets may function as one-way check valves that open to allow blood flow in a desired direction. The leaflets may also close in response to pressure differentials in order to limit reverse flow. Thus, when blood is flowing downstream, the leaflets may fully open to allow for flow through the valve. The leaflets may also correspondingly close to inhibit flow upstream. For aortic and pulmonary valves, the valves may open to permit blood flow from the heart into the arteries and may close to resist flow back from the arteries to the heart.

Figure 1:
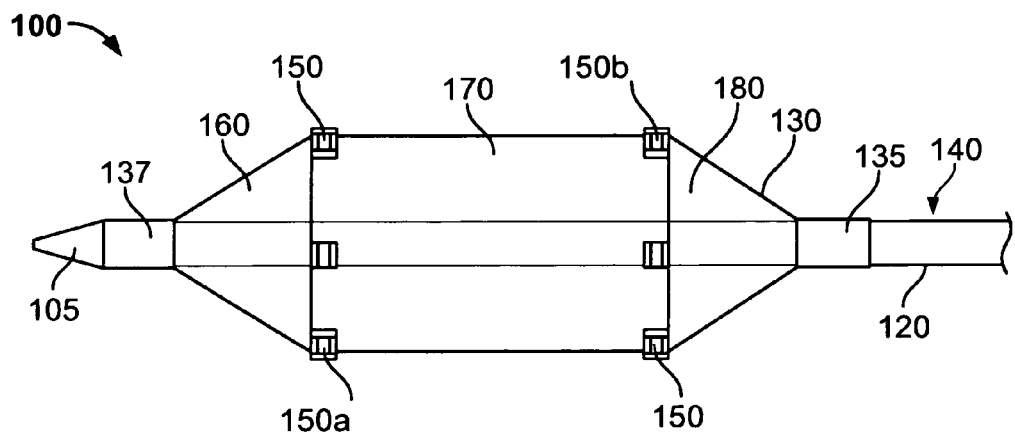
FIG. 1 is a partial side elevational view of a delivery catheter with an expanded balloon having a retaining mechanism in accordance with a first exemplary embodiment of the invention.

Stent 810 may be inserted into the body, moved to a deployment site, and deployed using a delivery catheter, such as a balloon catheter. The distal end of one such balloon catheter 100 is shown in FIG. 1. Catheter 100 includes a balloon 130 which is connected to catheter body 140 at a proximal seal 135 and a distal seal 137. The balloon 130 may be connected to catheter body 140 by any known method, for example, by chemical or mechanical welding to the proximal and distal seals 135, 137. Although not completely depicted in FIG. 1, catheter body 140 may extend from a distal tip 105 to a proximal end which remains outside of the body. The proximal end may be connected to a liquid source, such as an incompressible liquid with a radiopaque contrast, for inflating the balloon. Distal tip 105 may also be tapered to help guide catheter 100 through a body lumen to the deployment site.

Balloon 130 is shown in FIG. 1 in a fully inflated or expanded condition. However, during the insertion of catheter 100, balloon 130 is in an uninflated or collapsed condition. Balloon 130 may be placed in the collapsed condition (not shown) by folding the balloon in any manner, for example, using a pleat fold or a T-fold. Balloon 130 may have a first tapered end portion 160, a middle portion 170, and a second tapered end portion 180, all of which can be readily seen in the expanded condition of FIG. 1.

As noted above, catheter 100 may be used to deploy prosthetic valves including stents having fully expanded diameters of up to about 30 mm. Once the balloon is deflated, the stent may recoil a few millimeters, for example 1-2 mm. Thus, the stent may actually be slightly smaller after being implanted. Accordingly, a stent expanded to about 30 mm may recoil to about 27 mm. Accordingly, to fully expand these valve stents into firm engagement with structures in and around the heart, balloon 130 may expand to a diameter of up to about 30 mm.

In its fully expanded condition, the middle portion 170 of balloon 130 may have a generally cylindrical cross-section, although other cross-sectional shapes are contemplated, including triangular, rectangular, trapezoidal, elliptical, curved, and other polygonal and non-polygonal shapes.

Stented valve 800 is assembled over balloon 130 for delivery. In one example, stented valve 800 in the expanded state may be positioned over the middle portion 170 of balloon 130 with the balloon in the uninflated or collapsed condition. Stented valve 800 may subsequently be collapsed into a compressed form around balloon 130. Various methods may be employed to collapse stented valve 800 around the balloon, such as hand tools or other mechanical or chemical methods. In another example, stented valve 800 may be at least partially collapsed prior to assembly over balloon 130. The at least partially collapsed valve may be maneuvered over the distal end 105 of balloon catheter 100 and positioned over middle portion 170 of balloon 130. The partially collapsed stented valve may then be further collapsed around the balloon.

Figure 2A:
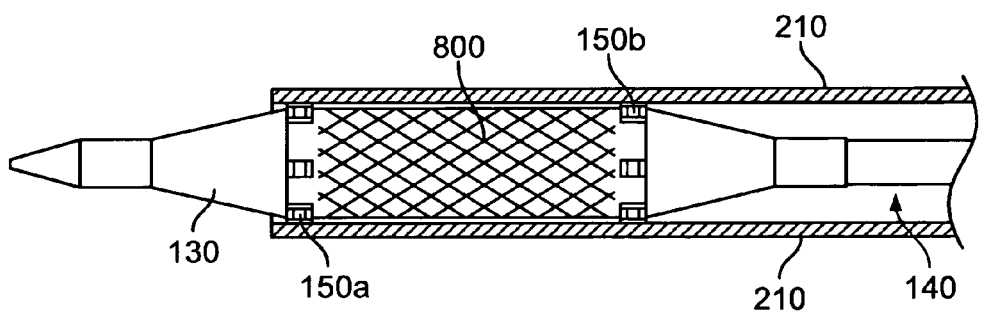
FIGS. 2A-2D are partial side elevational views showing a delivery method using the delivery catheter of FIG. 1.

Once the stented valve has been assembled over balloon 130 and placed in the collapsed condition, a sheath, such as sheath 210 of FIG. 2A, may be moved into position over the assembly. Sheath 210 may protect stented valve 800 and balloon 130 during the insertion of catheter 100 into and through the patient's vasculature, and at the same time prevent displacement of the valve relative to the balloon.

Once catheter 100 has been positioned at or near the native valve where stented valve 800 is to be implanted, sheath 210 may be withdrawn to reveal stented valve 800 and balloon 130. As noted above, after removal of the sheath 210 and prior to inflation of the balloon 130, various forces, such as the vibrations of a beating heart and the high velocity of blood flow within and immediately adjacent to the heart, may cause the valve to move relative to the balloon.

In order to retain stented valve 800 in its assembled position on balloon 130 once sheath 210 has been withdrawn, balloon 130 may be provided with a plurality of raised retainer nodes 150. As shown in FIG. 1, a first group of one or more retainer nodes 150a may be positioned at one end of the middle portion 170 of balloon 130, and a second group of retainer nodes 150b may be positioned at the other end of middle portion 170. Where each end of middle portion 170 includes more than one retainer node 150, the retainer nodes may be spaced either evenly or unevenly around the outer circumference of the middle portion.

It will be appreciated that retainer node groups 150a and 150b, shown in FIG. 2A, do not have to be at the ends of middle portion 170. Rather, they may be spaced apart in the longitudinal or axial direction of balloon 130 by a distance sufficient to accommodate the stent 810 of stented valve 800 fully therebetween. In that regard, node groups 150a and 150b may be spaced apart in the longitudinal direction so as to contact the ends of stent 810 in the collapsed condition and substantially prevent the stent from moving in the longitudinal direction relative to balloon 130. Alternatively, node groups 150a and 150b may be spaced apart by a distance greater than the length of stent 810 in the collapsed condition so that the stent may be free to move by a relatively small amount in the longitudinal direction in relation to balloon 130. While limiting movement in the longitudinal direction, the retainer nodes are not positioned in the stent cells 840 and therefore do not interfere with the full collapsing of the stent. Moreover, because of this positioning, the retainer nodes may allow the stent in the collapsed or expanded conditions to rotate on the balloon.

Nodes 150 may be of various shapes and sizes and may be either mounted to the outer surface of balloon 130 or formed integrally with the balloon, for example in a molding process with the balloon. Other examples of the formation of the retainer nodes may include a separate molding operation after the formation of the balloon, bonding the retainer nodes to the balloon surface, or a process commonly referred to as balloon grinding. Nodes 150 may be characterized as bumps, humps, raised protrusions, angular projections, or the like. As shown in FIG. 9, the size and shape of the nodes in one group, group 910, may be the same as or different from the size and shape of the nodes in the other group, group 920. Also, the nodes in one group need not all be of the same size and shape, but may be specifically sized and shaped relative to any features which may be present at the ends of stent 810. In all cases, however, nodes 150, both individually and collectively, define raised edges relative to the outer surface of the middle position 170 of the balloon that engage the free ends of stent 810 and limit the movement of valve 800 in the longitudinal direction relative to the balloon 130.

Nodes 150 may be generally rigid such that the nodes may protrude from the balloon regardless of whether the balloon is in a collapsed condition or an expanded condition. As balloon 130 expands, nodes 150 may move with the balloon and maintain their general form. When the balloon 130 is fully inflated, as shown in FIG. 1, the nodes 150 may continue to maintain their form, holding stent 810 in place therebetween. Once stent 810 has been properly positioned and fully expanded, it may be released from balloon 130 by deflating the balloon. As balloon 130 collapses, the balloon and nodes 150 may be withdrawn through the expanded stent 810 and valve leaflets 860.

Figure 2B:
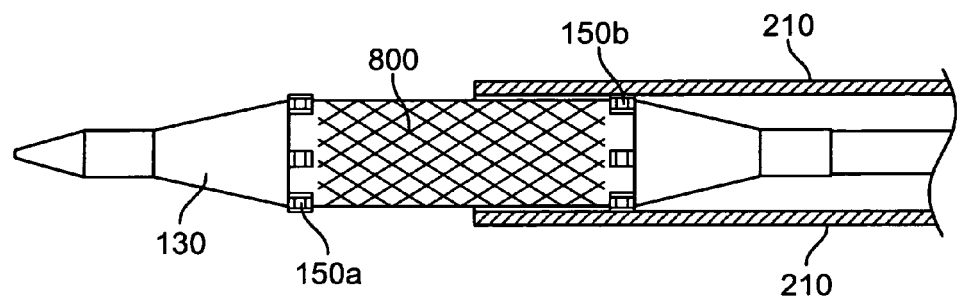
Figure 2C:
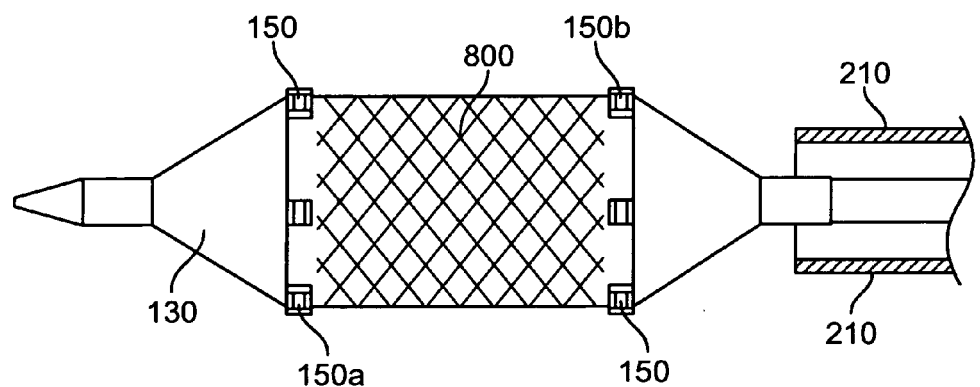

FIGS. 2A-2D depict an exemplary expansion of stented valve 800 using a balloon catheter 100 in which the balloon 130 includes retainer nodes 150. As shown in FIG. 2A, stented valve 800 is positioned on the balloon 130 such that the valve stent 810 is substantially centered on the middle portion 170 of the balloon and positioned axially between retainer nodes 150. Sheath 210 extends over the balloon 130 and stented valve 800 and prevents them from being subjected to forces that may change their relative positions. When catheter 100 has been advanced to a location in which stented valve 800 is substantially at the desired position in the body for deployment, sheath 210 may be withdrawn from its position over stented valve 800 and balloon 130 as depicted in FIG. 2B. Despite the turbulence and other movement artifacts to which stented valve 800 may be subjected at this point in the deployment, retainer nodes 150 may hold the valve securely in position on the uninflated balloon 130.

Figure 2D:
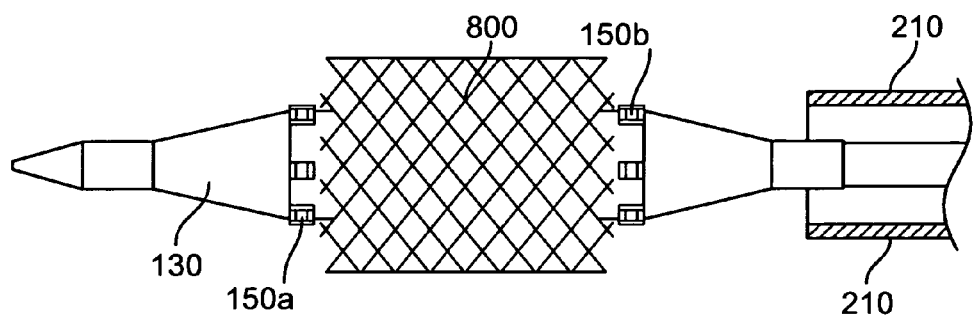

Once the accurate positioning of stented valve 800 has been confirmed, balloon 130 may be inflated, expanding stent 810 into a non-compressed geometry. As balloon 130 expands, retainer nodes 150 move radially outward with the balloon while continuing to project outwardly from the balloon surface. Hence, when balloon 130 has been fully inflated, retainer nodes 150 may still maintain the longitudinal position of stented valve 800 relative to the balloon and provide protection for the ends of valve stent 810. Therefore, as long as balloon catheter 100 is held firmly in place during valve deployment, the position of stented valve 800 will remain substantially unchanged and the valve will be deployed in the proper location. When deployment has been completed, balloon 130 may be deflated as shown in FIG. 2D and catheter 100 may be withdrawn from stented valve 800, leaving the valve in place.

Figure 3:
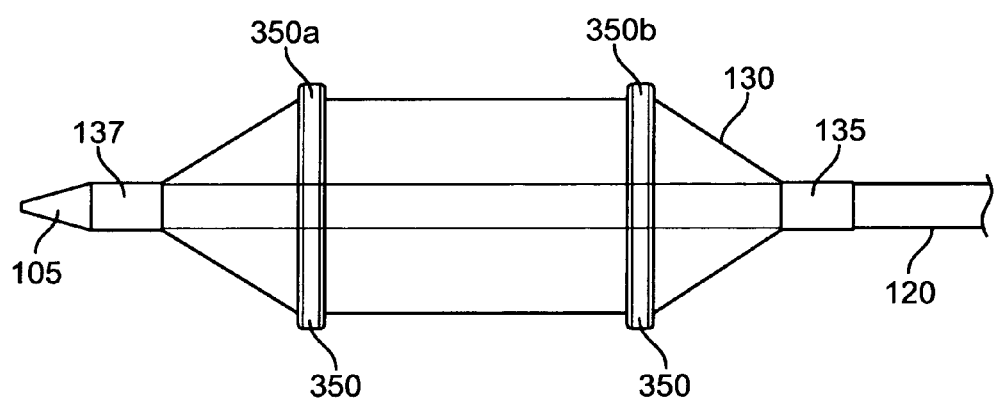
FIG. 3 is a partial side elevational view of a delivery catheter with an expanded balloon having a retaining mechanism in accordance with a second exemplary embodiment of the invention.

A retaining mechanism in accordance with a second embodiment of the present invention is shown in FIG. 3. The embodiment of FIG. 3 is substantially the same as the embodiment of FIG. 1 described above, except that retainer nodes 150 have been replaced with retainer rings 350. Similar to the function of retainer nodes 150, retainer rings 350 may form retainers which maintain their general form during the inflation of balloon 130 and prohibit movement of stented valve 800 longitudinally along the balloon prior to and during inflation.

Retainer rings 350 may be placed at each end of the middle portion 170 of balloon 130 to maintain the general position of the stented valve 800 along the balloon. As with nodes 150, retainer rings 350a and 350b, shown in FIG. 3, do not have to be at the ends of middle portion 170, but may be spaced apart by a distance sufficient to accommodate the stent 810 of stented valve 800 fully therebetween. In that regard, the distance between retainer rings 350a and 350b may be such that they either contact or do not contact the ends of stent 810, allowing little or no movement of the valve in relation to the balloon. As with nodes 150, the retainer rings do not interfere with the full collapsing of stent 810 and may allow the collapsed stent to rotate on the balloon.

Retainer rings 350a and 350b may be formed similarly to nodes 150 described above. For example, a ring may be mounted to the outer surface of balloon 130 or formed integrally with the balloon in a molding or grinding process. Retainer rings 350a and 350b may protrude above the surface of balloon 130 at the same or different heights depending on the requirements of stent 810. Further, the axial or circumferential thickness of each retainer ring 350a and 350b may be constant around balloon 130 or may vary to accommodate certain features of stent 810. In all cases, however, retainer rings 350a and 350b present raised edges which engage the ends of stent 810 and limit its movement in the longitudinal direction relative to the balloon.

As noted above, retainer rings 350 may expand elastically and continue to project outwardly from balloon 130 as the diameter of the balloon increases during inflation. When the balloon is fully inflated, as shown in FIG. 3, the rings 350 may continue to protrude from the surface of the balloon, providing end protection to stent 810 and maintaining the axial position of stented valve 800 on the delivery catheter. Once stented valve 800 has been deployed within the body lumen and fully expanded, balloon 130 may be deflated, allowing the valve to be released from the delivery catheter. The delivery catheter may be removed by withdrawing the balloon 130 and retainer rings 350 through the valve leaflets 860 and stent 810.

Figure 4:
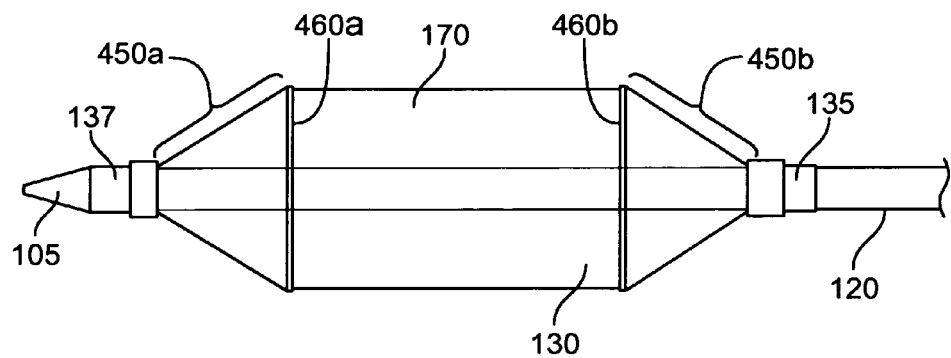
FIG. 4 is a partial side elevational view of a delivery catheter with an expanded balloon having a retaining mechanism in accordance with a third exemplary embodiment of the invention.

A retaining mechanism in accordance with a third embodiment of the present invention is shown in FIG. 4. In this embodiment, rather than nodes or rings on the circumference of middle portion 170 as in the previously described embodiments, balloon 130 is provided within a retainer skirt 450a or 450b on each of balloon end portions 160 and 180. Retainer skirts 450a and 150b may expand elastically during inflation of balloon 130 and continue to project outwardly from the balloon as the diameter of the balloon increases during inflation. A first skirt 450a on end portion 160 may protrude above the surface of the middle portion 170 to define an annular edge or lip 460a at one end of the middle portion. A second skirt 450b may protrude above the surface of the middle portion 170 to define an annular edge or lip 460b at the other end of the middle portion. As with the previous embodiments, lips 460a and 460b are spaced apart a sufficient distance to receive the stent 810 of stented valve 800 therebetween. Thus, lips 460a and 460b cooperate to maintain the position of stent 800 relative to balloon 130.

Similar to retainer nodes 150 and retainer rings 350, retainer skirts 450a and 450b may be separately formed and mounted to end portions 160 and 180, respectively, or may be formed by making the thickness of balloon 130 greater in end portions 160 and 180 than in middle portion 170. This increased thickness may be uniform from the proximal and distal seals 135, 137 to the middle portion 170. Alternatively the thickness may increase gradually from the seals 135, 137 toward the middle portion. Retainer skirts 450a and 450b may also be of different thicknesses and accordingly lips 460a and 460b may protrude above the balloon 130 at different radial distances circumferentially around the balloon.

Lips 460a and 460b may be positioned at each end of the middle portion of balloon in order contact or not contact the ends 820, 830 of the stented valve 800. Accordingly, lips 460a and 460b may prevent any axial movement relative to the balloon 130 or provide for only some small movement. Lips 460a and 46-b may function similarly to retainer nodes 150 and retainer rings 350, protruding outwardly from the balloon prior to and during inflation of the balloon and accordingly, providing end protection to the stent and preventing longitudinal movement of the stented valve 800 relative to the balloon 130. Again, once the stented valve 800 is fully expanded and positioned within the body lumen, the balloon may be deflated, and the catheter 100 removed through the valve leaflets 860 and stent 810.

Figure 5:
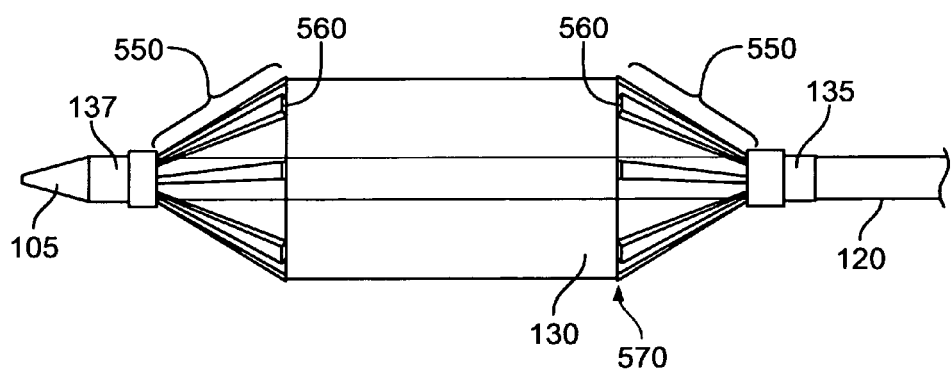
FIG. 5 is a partial side elevational view of a delivery catheter with an expanded balloon having a retaining mechanism in accordance with a fourth exemplary embodiment of the invention.

A retaining mechanism in accordance with a fourth embodiment of the present invention is shown in FIG. 5, in which retainer fan skirts 550 are provided. The retainer fan skirts 550 operate similarly to retainer nodes 150, retainer rings 350, and retainer skirts 450a and 450b described above, in that they may also be used to maintain the position of the valve on the delivery catheter prior to and during inflation of the balloon.

Retainer fan skirts 550 preferably comprise one or more ridges 560. Similar to the embodiments described above, ridges 560 may be mounted to or formed from the balloon material and may be evenly or unevenly spaced around the circumference of balloon 130 and of various shapes and sizes. Two or more ridges within the same fan skirt may have different shapes and thicknesses. Accordingly, if more than one retainer fan skirt 550 is used, the skirts may have different shapes and dimensions.

Ridges 560 may extend from the proximal and distal seals 135 and 137 to the middle portion 170. Ridges 560 may also continue along some length of the middle portion 170 and terminate in protruding bumpers 570 which may both provide end protection to the stent and prevent or limit longitudinal movement of the stented valve 800 relative to the balloon. Ridges 560 may terminate such that the bumpers are positioned along the balloon 130 to contact both ends 820, 830 of the stented valve 800 and prohibit any movement of the stented valve 800 in the longitudinal or axial direction along the balloon. The bumpers 570 may also terminate so as to contact one end or neither end of the stented valve 800, and therefore allow limited longitudinal movement of the stented valve 800 relative to the balloon 130. Nonetheless, the ridges 560 do not interfere with the full collapsing of the stent 810 and may allow the collapsed stent to rotate on the balloon.

As the balloon 130 is inflated, the retainer fan skirts 550 may expand with the balloon and both the ridges 560 and bumpers 570 may continue to protrude above the surface of the balloon. When the balloon 130 is fully inflated, as shown in FIG. 5, the bumper protrusions 570 may continue to maintain the general position of the valve on the delivery catheter. Finally, once in position, the valved stent 800 may be released by deflating the balloon 130, and the catheter 100 may be removed through the stent 810 and the valve leaflets 860.

Figure 6:
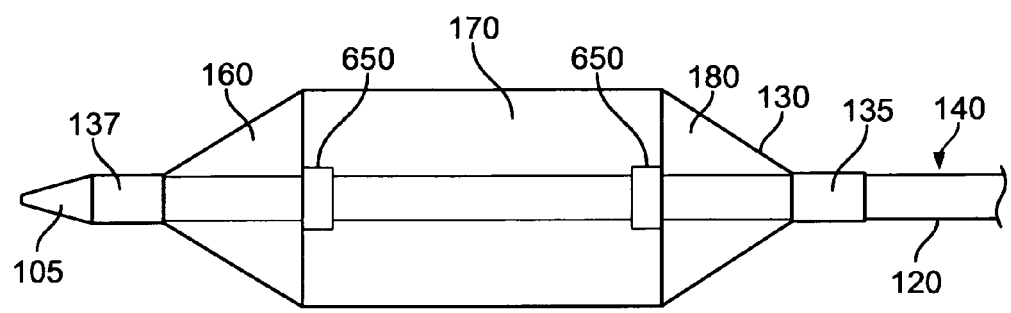
FIG. 6 is a partial side elevational view of a delivery catheter with an expanded balloon having a retaining mechanism in accordance with a fifth exemplary embodiment of the invention.

A retaining mechanism in accordance with a fifth embodiment of the present invention is shown in FIG. 6. In this embodiment, retainer bulges 650 may be used to maintain the position of the valved stent relative to the balloon 130 prior to and during expansion of the balloon.

As shown in FIG. 6, two retainer bulges 650 may be positioned at each end of the middle portion 170 of the balloon 130. The retainer bulges 650 may be integrated on the inner lumen 120 of the delivery device by thermal or adhesive bonding. When mounted to the inner lumen 120, bulges 650 may be rigid, and may maintain their general configuration before and during inflation. In an alternative, retainer bulges 650 may be mounted to or formed on an inner surface of balloon 130. The retainer bulges may be elastic so as to expand as the balloon is expanded. The retainer bulges 650 may be configured of any material, for example, metal or plastic, but are preferably a polymer.

Figure 7:
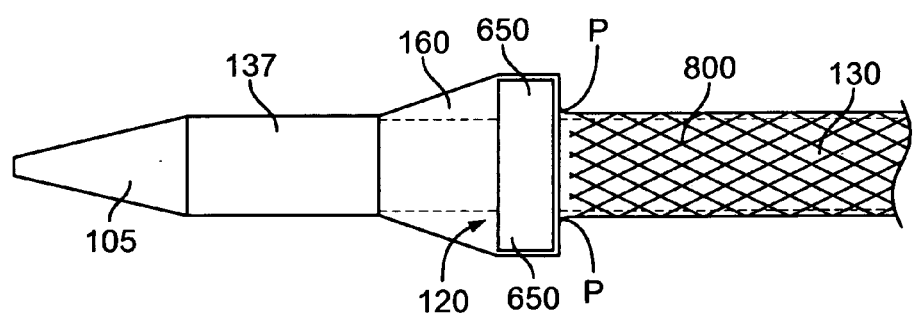
FIG. 7 is a partial side elevational view of a delivery catheter with an at least partially unexpanded balloon having a retaining mechanism in accordance with the fifth exemplary embodiment of the invention.

As shown in FIG. 7, the valved stent 800 may be placed along the uninflated balloon 130 to contact the balloon material between the stented valve 800 and the retainer bulge 650 at a pinch point P. As the balloon expands, retainer bulges 650 may maintain the position of the stent by prohibiting any or substantially all movement of the stented valve 800 in the longitudinal or axial direction along the balloon until the expanded diameter of the balloon is greater than the diameter of the retainer bulge. At this point, the stented valve 800 may have also expanded to a diameter greater than the diameter of the retainer bulge so as to no longer be retained between the bulges. The stented valve 800 may continue to be expanded by the balloon 130 and placed in position against the body lumen. Balloon 130 may be deflated and catheter 100 may be removed through the stent 810 and the valve leaflets 860. It will be appreciated that, as with the other embodiments described above, the retainer bulges 650 do not interfere with the full collapsing of the stent 810 on the balloon, and may allow the collapsed stent to rotate on the balloon.

Most of the foregoing alternative embodiments are not mutually exclusive, but may be implemented in various combinations to achieve unique advantages. For example, one end of the balloon may include a particular retainer arrangement while the other includes a second. As these and other variations and combinations of the features discussed above can be utilized without departing from the invention as defined by the claims, the foregoing description of the embodiments should be taken by way of illustration rather than by way of limitation of the invention as defined by the claims. It will also be understood that the provision of examples of the invention (as well as clauses phrased as "such as," "including" and the like) should not be interpreted as limiting the invention to the specific examples; rather, the examples are intended to illustrate only one of many possible embodiments.

The invention claimed is:

1. A delivery system for a prosthetic valve, the delivery system comprising:
   a valve structure mounted to a stent structure, the stent structure having a collapsed condition, an expanded condition, and a length in the collapsed condition between a first end and a second end;
   a balloon extending in a longitudinal direction and having a first tapered end portion, a second tapered end portion and a middle portion between the first tapered end portion and the second tapered end portion, the middle portion having an outer surface with a first diameter in a fully inflated condition and a second diameter in a deflated condition;
   an inflation lumen connected in fluid communication to an interior of the balloon for supplying an inflation fluid to the balloon; and,
   first and second retainer structures attached to an outer surface of only the middle portion, each of the first and second retainer structures defining a raised edge relative to the outer surface of the middle portion, the raised edges being spaced apart in the longitudinal direction to define a receiving space around the middle portion of the balloon, the receiving space having a length in the longitudinal direction which is greater than the length of the stent structure in the collapsed condition so that the entire length of the stent structure in the collapsed condition is receivable in the receiving space,
   wherein the raised edges allow for limited movement of the stent structure in the longitudinal direction relative to the balloon both when the stent structure is in the collapsed condition and the balloon is in the deflated condition and when the stent structure is in the expanded condition and the balloon is in the fully inflated condition, the raised edges being configured to maintain their shape when the balloon is inflated from the deflated condition to the fully inflated condition, and
   wherein the raised edges are configured to no longer limit movement of the stent structure in the longitudinal direction relative to the balloon after the balloon is deflated from the fully inflated condition to the deflated condition and the stent structure is in the expanded condition, and the first retainer structure is of a first type and the second retainer structure is of a second type different from the first type.

2. The delivery system of claim 1, wherein the first retainer structure is of a type selected from the group consisting of a node, a ring, a skirt, and a fan skirt.

3. The delivery system of claim 2, wherein the second retainer structure is of a type selected from the group consisting of a node, a ring, a skirt, and a fan skirt.

4. The delivery system of claim 1, wherein the raised edges are positioned relative to the middle portion to limit movement of the stent structure in the longitudinal direction relative to the balloon during inflation of the balloon from the deflated condition to the inflated condition.

5. The delivery system 1, further comprising:
a first group of retainer structures of the first type defining raised edges at a first end of the receiving space, wherein the first retainer is included in the first group; and
a second group of retainer structures of the second type defining raised edges at a second end of the receiving space opposite of the first end of the receiving space, wherein the second retainer is included in the second group.

6. The delivery system of claim 5, wherein the first group of retainers are of a first type of node having a first size and a first shape, and the second group of retainers are of a second type of node having a second size different from the first size, the second type of node having a second shape different from the first shape.

7. The delivery system of claim 5, wherein the first group of retainers include nodes that are not all of a same size and shape.

8. The delivery system of claim 1, wherein the raised edges are configured to allow for rotational movement of the stent structure in the collapsed condition.

9. A method of delivering a prosthetic valve to an implantation site, the prosthetic valve having a valve structure mounted to a stent structure, the stent structure having a collapsed condition, an expanded condition, and a length in the collapsed condition between a first end and a second end, the method comprising:
assembling the valve around a balloon having a fully inflated condition and a deflated condition, the balloon extending in a longitudinal direction and having a first tapered end portion, a second tapered end portion and a middle portion between the first tapered end portion and the second tapered end portion, the balloon having an outer surface and first and second retainer structures attached to the outer surface of only the middle portion and each of the first and second retainer structures defining a raised edge relative to the outer surface of the middle portion, the raised edges being spaced apart in the longitudinal direction to define a receiving space between the first and second tapered end portions, the first retainer structure is of a first type to accommodate a first end of the stent and the second retainer structure is of a second type different from the first type to accommodate a second end of the stent, the receiving space having a length in the longitudinal direction which is greater than the length of the stent structure in the collapsed condition, the valve being assembled in the receiving space so that the stent structure is in the collapsed condition and the balloon is in the deflated condition;
covering the valve in the collapsed condition and the balloon in the deflated condition with a sheath;
moving the covered valve and balloon to an implantation site;
removing the sheath from over the valve and the balloon to expose the valve and the balloon, whereby the valve is held in the receiving space and the raised edges allow for limited movement of the stent structure in the collapsed condition in the longitudinal direction relative to the balloon;
inflating the balloon to the fully inflated condition, whereby the stent structure of the valve is expanded to the expanded condition and the raised edges continue to limit movement of the stent structure in the longitudinal direction relative to the balloon, the raised edges being configured to maintain their shape while the balloon is inflated to the fully inflated condition;
after inflating the balloon to the inflated condition, deflating the balloon in order to release the stent structure from the receiving space so that the raised edges no longer limit movement of the stent structure in the longitudinal direction relative to the balloon; and
removing the deflated balloon from the stent structure.

10. The method of claim 9, wherein removing the deflated balloon includes withdrawing the retainer structures through a lumen of the stent structure.

11. The method of claim 9, wherein the first retainer structure is of a type selected from the group consisting of a node, a ring, a skirt, and a fan skirt.

12. The method of claim 9, wherein the second retainer structure is of a type selected from the group consisting of a node, a ring, a skirt, and a fan skirt.

13. The method of claim 9, wherein the raised edges are configured to allow for rotational movement of the stent structure in the collapsed condition.

* * * * *